United States Patent [19]
Castor

[11] Patent Number: 5,531,096
[45] Date of Patent: Jul. 2, 1996

[54] GAS ANALYZER AND METHOD FOR ANALYZING A GAS

[75] Inventor: Rolf Castor, Haegerstein, Sweden

[73] Assignee: Siemens Elema AB, Solna, Sweden

[21] Appl. No.: 342,058

[22] Filed: Nov. 17, 1994

[30] Foreign Application Priority Data

Dec. 3, 1993 [SE] Sweden ................... 9304028

[51] Int. Cl.[6] .............. G01N 30/00; G01N 31/00; A61B 5/08
[52] U.S. Cl. .................. 73/23.2; 73/23.3; 73/863; 73/864.81; 73/29.02
[58] Field of Search .................. 73/23.20, 23.24, 73/23.30, 23.42, 863, 863.02, 864.81, 29.02; 128/719

[56] References Cited

U.S. PATENT DOCUMENTS

| | | | |
|---|---|---|---|
| 3,861,195 | 1/1975 | vom Hagen | 73/23 |
| 4,109,509 | 8/1978 | Cramer et al. | 73/23 |
| 4,150,670 | 4/1979 | Jewett et al. | 128/188 |
| 4,169,465 | 10/1979 | Walls et al. | 128/719 |
| 4,202,352 | 5/1980 | Osborn | 128/719 |
| 4,441,356 | 4/1984 | Bohl | 73/23 |
| 4,459,994 | 7/1984 | Slemeyer | 128/719 |
| 4,476,708 | 10/1984 | Baker et al. | 73/23 |
| 4,509,359 | 4/1985 | Gedeon et al. | 73/23 |
| 4,619,269 | 10/1986 | Cutter et al. | 128/719 |
| 4,756,670 | 7/1988 | Arai | 417/43 |
| 5,069,220 | 12/1991 | Casparie et al. | 128/719 |
| 5,187,972 | 2/1993 | DeFriez | 73/23.2 |
| 5,398,695 | 3/1995 | Anderson et al. | 128/719 |

Primary Examiner—Hezron E. Williams
Assistant Examiner—J. David Wiggins
Attorney, Agent, or Firm—Hill, Steadman & Simpson

[57] ABSTRACT

A method for gas analysis includes the steps of extracting a gas sample from a gas to be analyzed with respect to one or more of its gas components, measuring the flow of the extracted gas sample, and adding a replacement gas to the gas in the same amount as the extracted sample in order to minimize the impact on the main gas flow of the extraction of the gas sample. The replacement gas can consist of the same gas components constituting the gas sample. A gas analyzer for performing the method is also disclosed.

17 Claims, 1 Drawing Sheet

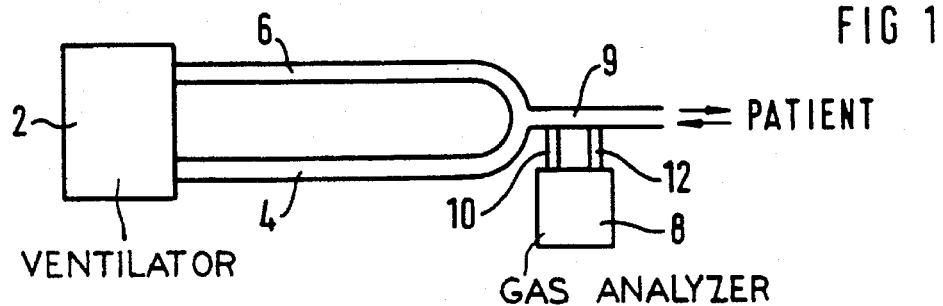
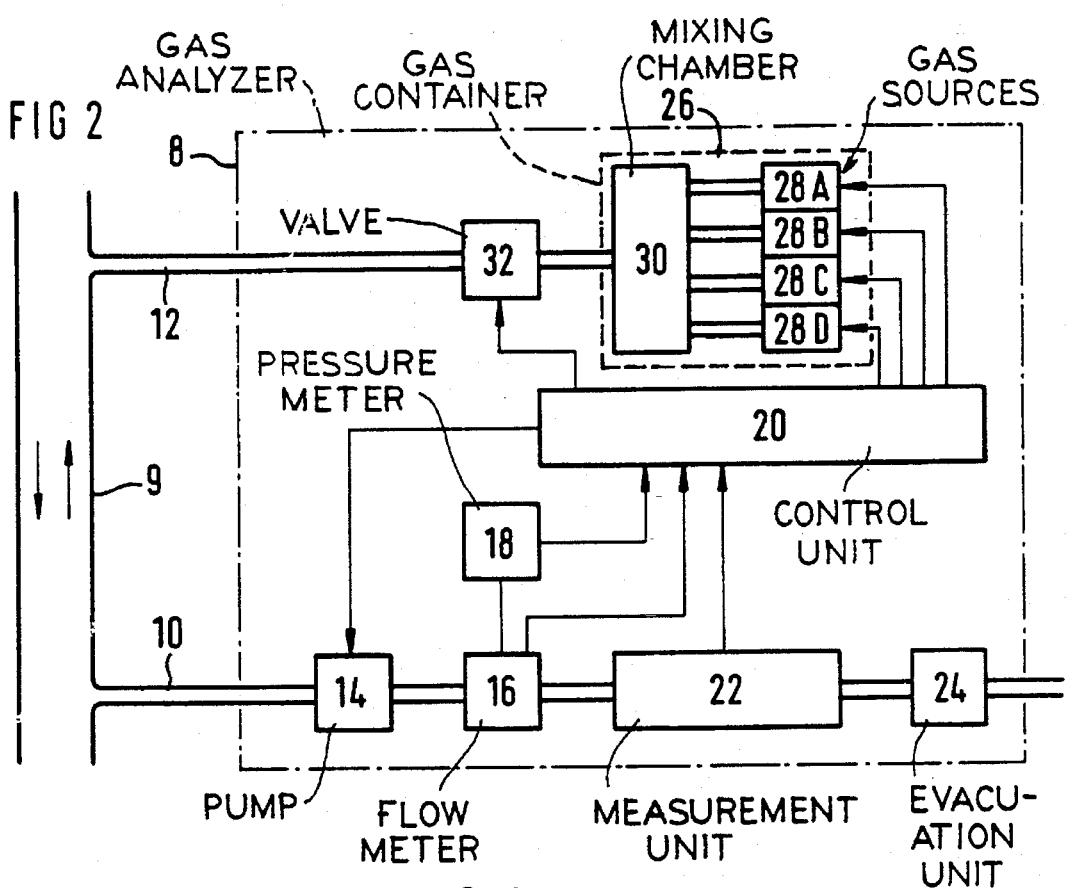
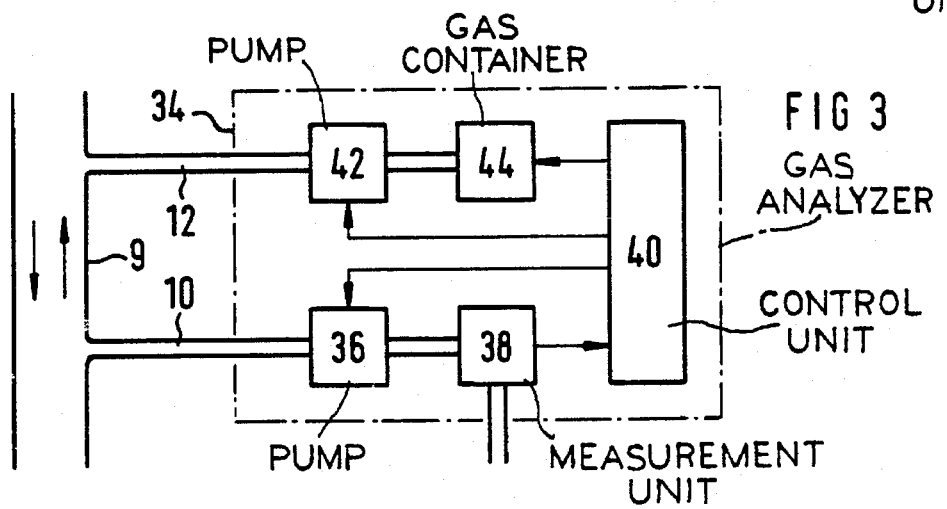

GAS ANALYZER AND METHOD FOR ANALYZING A GAS

BACKGROUND OF THE INVENTION

1. Field of the Invention

The present invention relates to a gas analyzer and a method for the analysis of a gas with respect to one or more gaseous components of the gas of the type wherein a gas sample is diverted from a gas to be analyzed.

2. Description of the Prior Art

When a gas is to be analyzed, a sample of the gas is commonly diverted to a measuring unit, e.g., a gas analyzer. One such method and gas analyzer are described in U.S. Pat. No. 4,509,359. This patent describes a method in which a continuous gas sample is diverted from a breathing gas during the ventilation of a patient's lungs. The gas sample is sent to a gas analyzer in which the concentration of, e.g., carbon dioxide or the like is determined. The gas sample is then discharged into ambient air or a collection container.

Modern ventilators and respirators, such as, e.g., the Servo Ventilator 300 from Siemens-Elema AB, Sweden, are able to control flows to/from a patient with great accuracy. They are also capable of regulating very small flows, a necessity, e.g., in the treatment of neonatal infants. With these ventilators, the removal of even a small gas sample will affect the flow to the patient and, in particular, will affect the regulation of inspiratory and expiratory flows.

Gas analyzers wherein a gas sample is extracted from the breathing gas and then returned to the breathing gas after measurement are known in the art. Some analysis procedures, however, can affect and alter one or more of the component gases. For example, oxygen can be measured with a high-temperature electrochemical cell. Any anaesthetic gases mixed with the breathing gas might then be chemically altered. In such a case, the analyzed gas cannot be returned to the breathing gas.

SUMMARY OF THE INVENTION

An object of the invention is to set provide a method gas analysis which permits a gas sample to be diverted from a gas flow and analyzed without altering the content and volume of the gas which reaches the destination of the gas flow.

The above object is achieved in accordance with the invention in a method wherein the flow of the diverted gas sample is measured and a replacement gas is added to the gas with substantially no (i.e., minimum) delay and in the same quantity as the diverted gas sample.

In this manner, the amount of the breathing gas in a ventilator is not affected when a gas sample for analysis is extracted from the breathing gas, e.g., during ventilation of a patient's lungs. The control of the inspiratory and expiratory flows will therefore not be affected, nor is there any risk of a chemically altered gas component being returned to the breathing gas.

In an embodiment of the method in accordance with the invention the pressure of the diverted gas is measured, the replacement gas is supplied at a predetermined pressure and the supply of replacement gas is regulated on the basis of the flow and pressure of the diverted gas.

The volume of a gas can be more accurately determined from the flow, if the pressure is taken into account as well. In particular, if the pressure of the gas sample flow varies, the flow of a replacement gas having a predetermined pressure will have to vary in order to supply the same amount of gas extracted, even if a constant gas sample flow is extracted.

In this context, it is advantageous if the replacement gas is prepared with the same gas components contained in the gas sample. Even if the gas sample is small and the impact of the replacement gas on the composition of the breathing gas is accordingly slight, this effect is reduced when the replacement gas contains the same gas components as the gas sample.

This is particularly advantageous when the gas sample is analyzed for the concentration of one or more of its gas components, and the replacement gas is prepared with the measured gas component concentrations so it has the same gas composition as the gas sample.

A gas analyzer for performing the method in accordance with the invention includes a pump for diverting a gas sample from a gas and a measurement unit, through which the gas sample is passed for analysis of one or a plurality of its components, a flow meter for measuring the flow of the diverted gas sample, and a control device for generating a control signal controlling a gas replacement device. The gas replacement device includes a gas container containing a replacement gas and a valve connected between the gas and the gas container, whereby the control signal controls the valve so a flow of replacement gas, corresponding to the measured flow of the gas sample, is added to the gas with minimum delay.

In this context it is advantageous if the gas replacement device is an integral part of the gas analyzer.

In an embodiment of the gas analyzer in accordance with the invention a pressure meter is arranged at the flow meter to measure pressure at the flow measurement site, and the control device determines the quantity of gas in the gas sample on the basis of the measured flow and pressure and controls the gas replacement device so a quantity of replacement gas equal to the amount of gas determined in the gas sample is added to the gas from the gas container.

Measurement of pressure at the flow measurement site means that determination of the amount of gas, on the basis of the measured flow, can be compensated for the pressure at the flow measurement site.

It is advantageous if the gas container has a mixing chamber connected to a plurality of gas sources supplying at least some of the gas components in the gas, whereby the control device regulates the preparation of replacement gas in the mixing chamber.

In this context, it is advantageous for the control device to be connected to the measurement unit for determining the concentration of the analyzed gas components and for the control device to regulate the preparation of replacement gas in the gas container, so it has the same gas composition as the gas sample with respect to the analyzed gas components.

In another embodiment of the gas analyzer for performing the method in accordance with the invention, the gas analyzer further includes a second pump, coupled in parallel to the aforementioned pump, and a gas container, containing a replacement gas, connected to the second pump, whereby the second pump pumps the same quantity of replacement gas to the gas as the quantity (constituting the gas sample) diverted by the aforementioned pump.

This results in a simply designed but simultaneously effective and functional gas analyzer.

DESCRIPTION OF THE DRAWINGS

FIG. 1 shows a gas analyzer constructed in accordance with the principles of the present invention and for performing the inventive method connected to a ventilator system.

FIG. 2 shows a gas analyzer constructed in accordance with the principles of the present invention and for performing the inventive method, in greater detail, in the form of a block diagram.

FIG. 3 shows a second embodiment of a gas analyzer constructed in accordance with the principles of the present invention and for performing the inventive method.

DESCRIPTION OF THE PREFERRED EMBODIMENTS

FIG. 1 shows a ventilator 2 which, via an inspiratory line 4, supplies a breathing gas to a patient. Gas expired by the patient is sent via an expiratory line 6 back to the ventilator 2, from which it can be discharged into the ambient atmosphere. A gas analyzer 8 is connected to a common inspiratory and expiratory line 9 through which breathing gas from the inspiratory line 4 is fed to the patient, and expiratory gas from the patient is sent to the expiratory line 6. The gas analyzer 8 extracts a gas sample from the common inspiratory and expiratory line 9 through a diversion line 10. A replacement gas is simultaneously sent to the common inspiratory and expiratory line 9 through a feed line 12.

The gas analyzer 8 can include e.g., an oxygen meter containing a high-temperature electrochemical cell.

FIG. 2 shows the gas analyzer 8 in greater detail. A pump 14 extracts the gas sample from the common inspiratory and expiratory line 9. The gas sample then passes a flow meter 16 which measures the flow of the gas sample. A pressure meter 18 is also connected near the flow meter 16 to measure the pressure at the flow measurement site. This is in order to determine the gas quantity of the gas sample so that compensation for its diversion from the main gas flow can be made. Respective electrical signals corresponding to the measured gas flow and the measured pressure are sent to a control unit 20, which determines how much gas the pump 14 has extracted from the common inspiratory and expiratory line 9.

The control unit 20 can also control the pump 14. For example, the control unit 20 can regulate the size of the gas sample, pumping effect and sampling intervals.

After passing the flow meter 16, the gas is fed into a measurement unit 22 in which, in this instance, the oxygen content of the gas sample is determined. A measurement signal corresponding to the oxygen content is sent to the control unit 20. The gas sample is then removed via a gas evacuation unit 24. Depending on the gas components in the breathing gas, the evacuation unit 24 can either discharge the gas sample directly into ambient air, filter out undesirable gases, or store the gas sample in an evacuation chamber.

In addition to determining the oxygen content of the gas sample, the control unit 20 can control replacement gas feed to the common inspiratory and expiratory line 9. A gas container 26, having a mixing chamber 30 and four gas sources 28A–D, is controlled by the control device 20 to prepare a replacement gas containing a plurality of different gas components. In particular, the replacement gas can consist of the gas components in the breathing gas. Here, the replacement gas is prepared so it has the same oxygen content as in the measured gas sample. This is particularly desirable in inspiration when the gas is supplied to the patient. In expiration, the replacement gas can consist of atmospheric air, since maintenance of the same quantity of gas in the system is then more important to the control function of the ventilator 2 than maintenance of the same gas composition.

Via a valve 32, the control unit 20 regulates the supply of replacement gas through the feed line 12 to the common inspiratory and expiratory line 9. The replacement gas is preferably kept at a constant pressure and the flow of replacement gas through the valve 32 is varied so the amount of replacement gas fed to the common inspiratory and expiratory line 9 is equal to the amount of the extracted gas sample.

The gas analyzer 8 can advantageously be integrated in whole or in part into the ventilator 2 or be devised as a separate, connectable gas replacement device.

FIG. 3 shows a gas analyzer 34 in a second embodiment of the invention. A gas sample is diverted from the common inspiratory and expiratory line 9 when a first pump 36 extracts gas through the diversion line 10. The gas sample is sent to a measurement device 38 in which one or more of its gas components is/are analyzed. The measurement signal is sent to a control unit 40.

Parallel to the first pump 36, a second pump 42 is arranged to pump a replacement gas back to the common inspiratory and expiratory line 9 from a gas container 44 via a feed line 12.

The pumps 36 and 42 are coupled to operate in parallel and pump the same quantity of gas. The pumps 36 and 42 are controlled by the control unit 40. The gas container 44 can be devised as the gas container 26 in the embodiment of FIG. 2, and composition of the gas mixture is controlled by the control unit 40.

The invention is not limited to use in conjunction with the ventilation of a patient's lungs. The ventilator 2 may be an anesthesia administration system or the like, or a more or less closed gas system in which a gas sample is extracted from the gas for analysis.

The gas analyzers 8 and 34 can be devised so the replacement gas either contains all the gas components in the analyzed gas, or only some of these gas components. In an anesthesia system, for example, the replacement gas can consist of nitrous oxide and oxygen in predetermined proportions, whereas the breathing gas also contains anesthetic gas.

The measurement units 22 and 38 can include measurement equipment for measuring a plurality of gas components. The measurement units 22 and 38 are not limited to measuring only the concentration of certain gas components. They may also include analysis equipment for identifying various unknown gases in the gas sample. Identification can also be made to ensure that a specific gas is present.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for analyzing a gas in a confined system with fluid flow having a plurality of gas components, with regard to at least one of said components, said method comprising the steps of:

extracting a quantity of gas from gas to be analyzed as a gas sample;

measuring the flow of said extracted gas sample; and supplying a replacement gas that compensates for said extracted quantity of gas back to said gas to be analyzed with substantially no delay following extraction of said gas sample and with said replacement gas having the same quantity as the extracted gas sample.

2. A method as claimed in claim 1 comprising the additional step of measuring the pressure of said extracted gas sample, and wherein the step of supplying said replacement gas is further defined by supplying said replacement gas at a predetermined pressure and the regulating the supply of said replacement gas dependent on the measurement of the flow and pressure of said extracted gas sample.

3. A method as claimed in claim 2 wherein the step of supplying said replacement gas comprises supplying a replacement gas having the same gas components as said extracted gas sample.

4. A method as claimed in claim 3 comprising the additional steps of:
analyzing said extracted gas sample to identify the concentration of its gas components, and wherein the step of supplying said replacement gas includes the step of preparing said replacement gas having a gas composition corresponding to the gas components measured in said extracted gas sample.

5. A method as claimed in claim 1 wherein the step of supplying said replacement gas comprises supplying a replacement gas having the same gas components as said extracted gas sample.

6. A method as claimed in claim 5 comprising the additional steps of:
analyzing said extracted gas sample to identify the concentration of its gas components, and wherein the step of supplying said replacement gas includes the step of preparing said replacement gas having a gas composition corresponding to the gas components measured in said extracted gas sample.

7. A gas analyzer for analyzing a gas with regard to at least one gas component of said gas, said analyzer comprising:
pump means for extracting a gas sample from a confined gas to be analyzed;
means, supplied with said gas sample by said pump means, for measuring a flow of said gas sample;
control means for generating a control signal dependent on the flow of said gas sample as measured by said means for measuring the flow;
a gas container containing a replacement gas; and
valve means, operable dependent on said control signal, for supplying a flow of replacement gas from said container to said confined gas with substantially no delay following extraction of said gas sample from said confined gas, and having a flow of said replacement gas corresponding to said flow of said gas sample.

8. A gas analyzer as claimed in claim 7 wherein said gas container and said valve means are formed as an integral unit together with said means for extracting said gas sample and said means for measuring the flow of said gas sample and said control means.

9. A gas analyzer as claimed in claim 8 wherein said means for measuring the flow of said gas sample measures said flow of said gas sample at a flow measurement site, and said gas analyzer further comprising pressure meter means for measuring a pressure of said gas sample at said flow measurement site, wherein said control means comprises means for generating said control signal dependent on the flow of said gas sample and dependent on the pressure of said gas sample, and wherein said valve means comprises means for regulating the flow of said replacement gas so that a quantity of said replacement gas corresponding to a quantity comprising said gas sample is supplied to said confined gas from said replacement gas container.

10. A gas analyzer as claimed in claim 9 wherein said replacement gas container comprises a mixing chamber and a plurality of gas sources connected to said mixing chamber, said gas sources respectively containing gases which are the same as at least some of said gas components of said gas sample, and wherein said control means comprises means for regulating mixing of said gases from the respective gas sources in said mixing chamber to produce said replacement gas.

11. A gas analyzer as claimed in claim 10 further comprising measurement means for determining a concentration of each gas component in said gas sample and for supplying a signal to said control means identifying said concentration, and wherein said control means comprises means for regulating the preparation of said replacement gas in said mixing chamber so that said replacement gas has the same gas composition as said gas sample with respect to the gas components identified in said measurement means.

12. A gas analyzer as claimed in claim 8 wherein said replacement gas container comprises a mixing chamber and a plurality of gas sources connected to said mixing chamber, said gas sources respectively containing gases which are the same as at least some of said gas components of said gas sample, and wherein said control means comprises means for regulating mixing of said gases from the respective gas sources in said mixing chamber to produce said replacement gas.

13. A gas analyzer as claimed in claim 12 further comprising measurement means for determining a concentration of each gas component in said gas sample and for supplying a signal to said control means identifying said concentration, and wherein said control means comprises means for regulating the preparation of said replacement gas in said mixing chamber so that said replacement gas has the same gas composition as said gas sample with respect to the gas components identified in said measurement means.

14. A gas analyzer as claimed in claim 7 wherein said means for measuring the flow of said gas sample measures said flow of said gas sample at a flow measurement site, and said gas analyzer further comprising pressure meter means for measuring a pressure of said gas sample at said flow measurement site, wherein said control means comprises means for generating said control signal dependent on the flow of said gas sample and dependent on the pressure of said gas sample, and wherein said valve means comprises means for regulating the flow of said replacement gas so that a quantity of said replacement gas corresponding to a quantity comprising said gas sample is supplied to said confined gas from said replacement gas container.

15. A gas analyzer as claimed in claim 14 wherein said replacement gas container comprises a mixing chamber with a plurality of gas sources connected to said mixing chamber, said gas sources respectively containing gases which are the same as at least some of said gas components of said gas sample, and wherein said control means comprises means for regulating mixing of said gases from the respective gas sources in said mixing chamber to produce said replacement gas.

16. A gas analyzer as claimed in claim 15 further comprising measurement means for determining a concentration of each gas component in said gas sample and for supplying a signal to said control means identifying said concentration, and wherein said control means comprises means for regulating the preparation of said replacement gas in said mixing chamber so that said replacement gas has the same gas composition as said gas sample with respect to the gas components identified in said measurement means.

17. A gas analyzer for analyzing a confined gas having a plurality of gas components, said gas analyzer comprising:

first pump means for extracting a gas sample from said confined gas;

means for analyzing said gas sample with regard to at least one of said gas components;

a source of replacement gas;

second pump means connected to said source of replacement gas for supplying said replacement gas to said confined gas; and means for operating said first pump means and said second pump means in parallel for causing said second pump means to pump a same quantity of replacement gas to said confined gas as said first pump means extracted from said confined gas as said gas sample.

* * * * *